United States Patent [19]

Summers

[11] Patent Number: 5,728,129

[45] Date of Patent: Mar. 17, 1998

[54] DISTAL ATHERECTOMY CATHETER

[75] Inventor: David P. Summers, Montgomery, Tex.

[73] Assignee: American Biomed, Inc., The Woodlands, Tex.

[21] Appl. No.: 478,984

[22] Filed: Jun. 7, 1995

Related U.S. Application Data

[63] Continuation-in-part of Ser. No. 895,099, Jun. 8, 1992, Pat. No. 5,431,673, which is a continuation-in-part of Ser. No. 833,362, Feb. 10, 1992, Pat. No. 5,370,651, which is a continuation of Ser. No. 383,606, Jul. 24, 1989, Pat. No. 5,087,265, which is a continuation-in-part of Ser. No. 312,737, Feb. 17, 1989, Pat. No. 4,994,067.

[51] Int. Cl.$^6$ ............................................. A61B 17/32
[52] U.S. Cl. ........................... 606/170; 606/159; 606/171
[58] Field of Search ........................ 606/159, 170, 606/171, 167, 177; 607/22

[56] References Cited

U.S. PATENT DOCUMENTS

| | | |
|---|---|---|
| Re. 33,569 | 4/1991 | Gifford, III ............................ 606/159 |
| 3,448,741 | 6/1969 | Dennis et al. . |
| 3,805,793 | 4/1974 | Wright . |
| 3,815,604 | 6/1974 | O'Malley et al. . |
| 3,844,272 | 10/1974 | Banko . |
| 3,882,872 | 5/1975 | Douvas et al. . |
| 3,884,238 | 5/1975 | O'Malley et al. . |
| 3,937,222 | 2/1976 | Banko . |
| 4,011,869 | 3/1977 | Seiler, Jr. . |
| 4,111,207 | 9/1978 | Seiler, Jr. . |
| 4,167,943 | 9/1979 | Banko . |
| 4,167,944 | 9/1979 | Banko . |
| 4,203,444 | 5/1980 | Bonnell et al. . |
| 4,210,146 | 7/1980 | Banko . |
| 4,273,128 | 6/1981 | Lary . |
| 4,323,071 | 4/1982 | Simpson et al. . |
| 4,411,055 | 10/1983 | Simpson et al. . |
| 4,513,745 | 4/1985 | Amoils . |
| 4,577,629 | 3/1986 | Martinez . |
| 4,589,412 | 5/1986 | Kensey . |
| 4,589,414 | 5/1986 | Yoshida et al. . |
| 4,598,710 | 7/1986 | Kleinberg et al. . |
| 4,603,694 | 8/1986 | Wheeler . |
| 4,616,648 | 10/1986 | Simpson et al. . |
| 4,616,652 | 10/1986 | Simpson et al. . |
| 4,631,052 | 12/1986 | Kensey . |
| 4,646,738 | 3/1987 | Trott . |
| 4,650,466 | 3/1987 | Luther . |
| 4,651,753 | 3/1987 | Lifton . |
| 4,661,094 | 4/1987 | Simpson et al. . |
| 4,662,869 | 5/1987 | Wright . |
| 4,669,649 | 6/1987 | Gifford, III et al. . |
| 4,678,459 | 7/1987 | Onik . |

(List continued on next page.)

FOREIGN PATENT DOCUMENTS 6155190  2/1991  Australia ............................ 606/159

*Primary Examiner*—Sam Rimell
*Assistant Examiner*—Luke J. Yeh
*Attorney, Agent, or Firm*—Nick A. Nichols, Jr.

[57] ABSTRACT

A distal atherectomy catheter is disclosed for removing obstructions, plaque, stenosis, occlusions, or the like from an artery or coronary vessel. The catheter comprises a flexible, hollow catheter tube. A cutting element is located within a cylindrical housing mounted at the distal end of the catheter tube. The cutting element is connected to a hollow, flexible drive shaft concentrically located within the catheter tube. The cutting element housing includes a side opening window or port providing access to the interior of the housing. An idler shaft journaled about the drive shaft provides a non-rotating surface adjacent the cutting element. An annular return passage is defined between the catheter tube and the flexible drive shaft providing a discharge passage communicating with external aspirating means for collection of cuttings removed by the cutting element from the artery or coronary vessel. A guide wire may extend through the catheter tube and cutting element for guiding the catheter to the occluded site in a vessel. The drive cable is connected to a drive motor housed within a handle housing. The catheter tube and cutter housing are enclosed within a sheath extending from the distal end of the catheter to the handle housing.

17 Claims, 5 Drawing Sheets

U.S. PATENT DOCUMENTS

| | | |
|---|---|---|
| 4,681,106 | 7/1987 | Kensey et al. . |
| 4,685,458 | 8/1987 | Leckrone . |
| 4,696,667 | 9/1987 | Masch . |
| 4,728,319 | 3/1988 | Masch . |
| 4,729,763 | 3/1988 | Henrie . |
| 4,747,406 | 5/1988 | Nash . |
| 4,747,821 | 5/1988 | Kensey et al. . |
| 4,749,376 | 6/1988 | Kensey et al. . |
| 4,765,332 | 8/1988 | Fischell et al. . |
| 4,771,774 | 9/1988 | Simpson et al. . |
| 4,772,258 | 9/1988 | Marangoni et al. . |
| 4,781,186 | 11/1988 | Simpson et al. . |
| 4,784,636 | 11/1988 | Rydell . |
| 4,794,931 | 1/1989 | Yock ................................ 606/159 |
| 4,819,635 | 4/1989 | Shapiro . |
| 4,834,729 | 5/1989 | Sjostrom . |
| 4,842,579 | 6/1989 | Shiber . |
| 4,844,064 | 7/1989 | Thimsen et al. . |
| 4,850,354 | 7/1989 | McGurk-Burleson et al. . |
| 4,857,045 | 8/1989 | Rydell . |
| 4,857,046 | 8/1989 | Stevens et al. . |
| 4,883,458 | 11/1989 | Shiber . |
| 4,895,560 | 1/1990 | Papantonakos . |
| 4,919,133 | 4/1990 | Chiang . |
| 4,926,858 | 5/1990 | Gifford, III et al. . |
| 4,979,951 | 12/1990 | Simpson . |
| 4,994,067 | 2/1991 | Summers ................................ 606/159 |
| 5,047,040 | 9/1991 | Simpson et al. . |
| 5,053,044 | 10/1991 | Mueller et al. . |
| 5,071,424 | 12/1991 | Reger . |
| 5,074,841 | 12/1991 | Ademovic et al. . |
| 5,084,010 | 1/1992 | Plaia et al. . |
| 5,085,662 | 2/1992 | Willard . |
| 5,087,265 | 2/1992 | Summers . |
| 5,092,873 | 3/1992 | Simpson et al. . |
| 5,100,425 | 3/1992 | Fischell et al. . |
| 5,100,426 | 3/1992 | Nixon . |
| 5,269,793 | 12/1993 | Simpson . |
| 5,370,651 | 12/1994 | Summers . |
| 5,409,454 | 4/1995 | Fischell ................................ 606/159 |
| 5,423,838 | 6/1995 | Willard . |

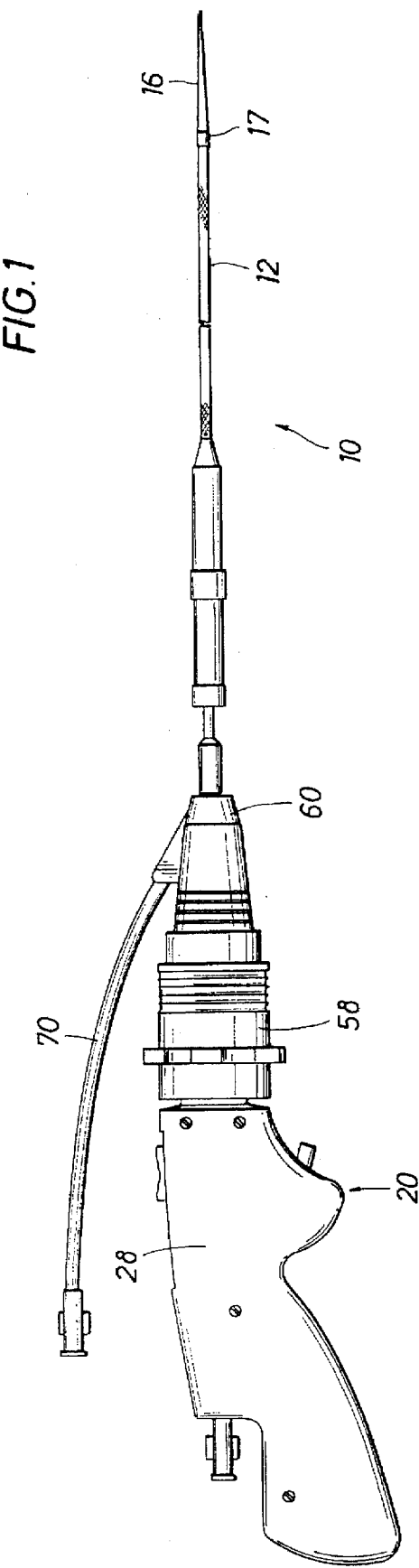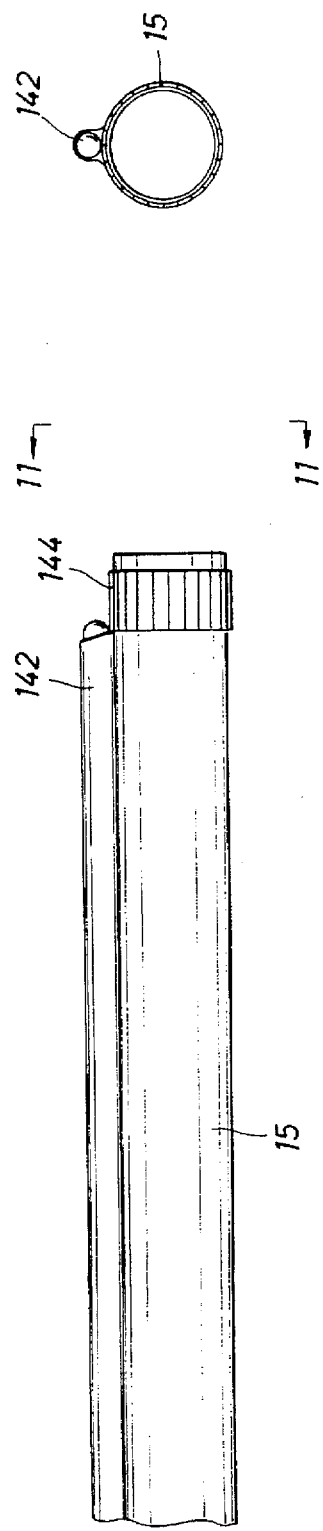
FIG. 1
FIG. 11
FIG. 10

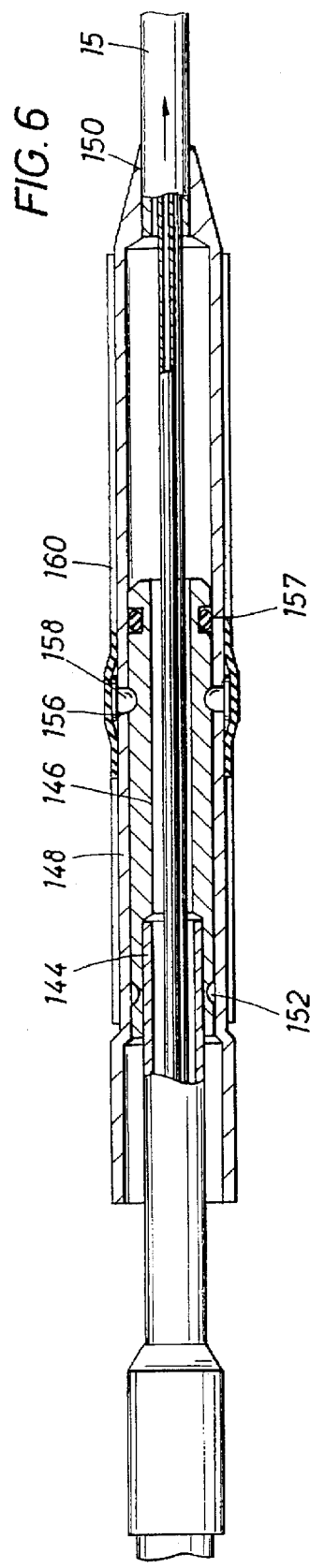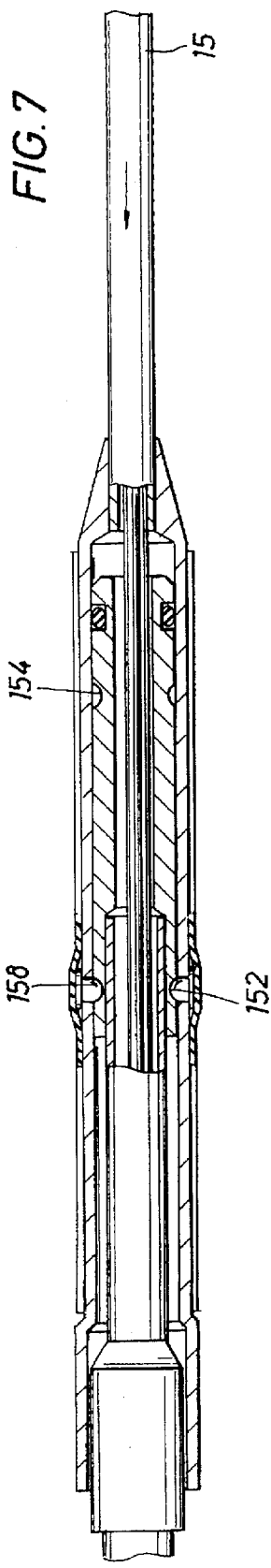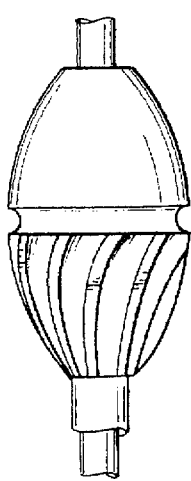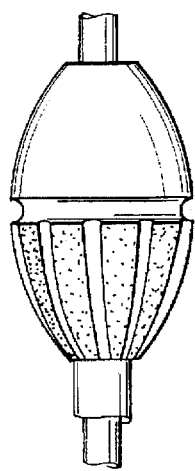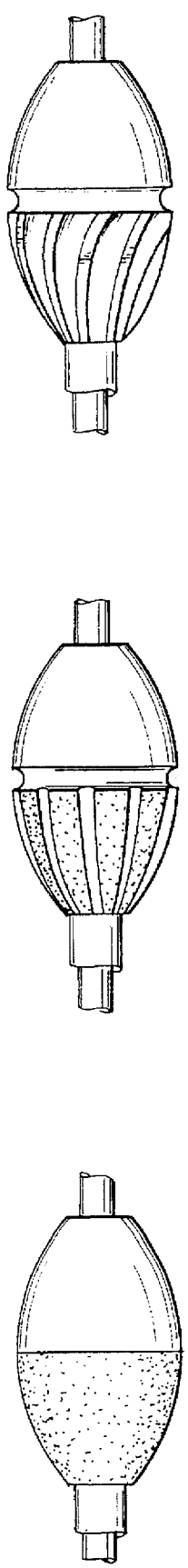

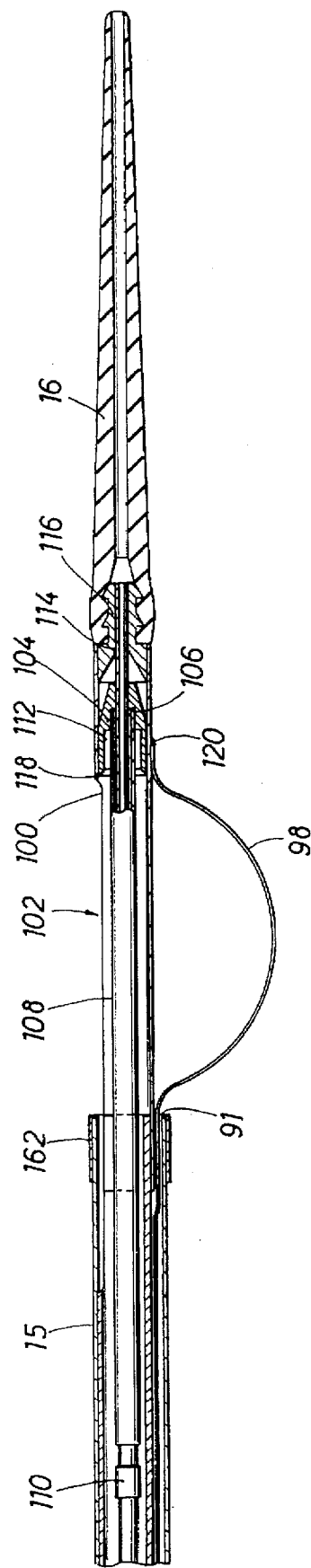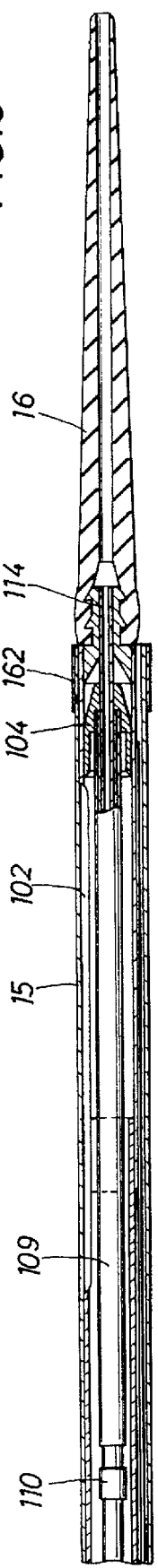

DISTAL ATHERECTOMY CATHETER

RELATED APPLICATIONS

This application is a continuation-in-part application of U.S. application Ser. No. 07/895,099 filed Jun. 8, 1992 issued as U.S. Pat. No. 5,431,673 on Jul. 11, 1995, which is a continuation-in-part application of U.S. application Ser. No. 07/833,362 filed Feb. 10, 1992, issued as U.S. Pat. No. 5,370,651 on Dec. 6, 1994, which is a continuation application of U.S. application Ser. No. 07/383,606, filed Jul. 24, 1989, issued as U.S. Pat. No. 5,087,265 on Feb. 11, 1992, which is an continuation-in-part application of U.S. application Ser. No. 07/312,737 filed Feb. 17, 1989, issued as U.S. Pat. No. 4,994,067 on Feb. 19, 1991.

BACKGROUND OF THE DISCLOSURE

The present invention is directed to an atherectomy catheter, particularly, a distal atherectomy catheter for use in the distal and coronary arteries where small vessel size and tortuosity present numerous problems of access.

Many technological advancements have been made in recent years for treatment of coronary disease. Surgical bypass techniques, such as coronary artery bypass graft surgery, are routinely performed and are highly successful. While the risks of bypass surgery have been minimized through technological advancements, opening of the chest cavity is still required. This requires special surgical skills and equipment which are not readily available in many areas. For many patients, a bypass operation may not be indicated and therefore various surgical techniques have been devised to treat occlusive coronary artery diseases of such patients. For example, various prior art devices have been developed for removing and/or compressing atherosclerotic plaque, thromboses, stenosis, occlusions, clots, embolic material, etc. from veins, arteries and the like.

One such device is disclosed in applicant's co-pending application Ser. No. 07/895,099 filed Jun. 8, 1992, which disclosure is incorporated by reference herein. In applicant's co-pending application, removal of occlusive material is accomplished by a reciprocal rotary cutter head mounted at the distal end of a catheter tube for excising occlusive material blocking the coronary vessel. While the apparatus of applicant's co-pending application has been successfully shown to remove occlusive material in laboratory tests, enhanced and more efficient removal of occlusive material may be achieved with the improved apparatus described herein.

U.S. Pat. No. 4,650,466 (Luther) discloses an angioplasty device comprising a woven tube of metal or plastic fibers and a retraction stylet that are attached at one end of the catheter tube for insertion into a vein, artery, and the like for the removal of plaque and similar materials. One or more guide wires are attached to the woven tube for rotation and manipulation inside the artery. The woven tube is placed within the artery and expanded to contact the interior, plaque coated, wall of the artery. Movement of the expanded tube abrades the plaque from the arterial wall to form particles which are trapped within the woven tubes. The trapped plaque particles are removed with angioplasty device upon its removal from the artery of the patient.

Other prior art devices include catheters fitted with an inflatable balloon for compressing occlusive materials such as plaque against the vessel wall. U.S. Pat. No. 4,273,128 (Lary) discloses a coronary cutting and dilating instrument for treatment of stenotic and occlusive coronary artery disease. The device disclosed therein includes a cutting and dilating instrument having one or more radially extending knife blades at a forward end thereof for making the coronary incision and an inflatable balloon for dilating the stenotic artery zone immediately after the incision.

Other angioplasty devices include a catheter having a motor driven cutting heat mounted at its distal end. The cutting head is connected to the drive motor via a flexible drive shaft extending through the catheter. Extremely high rotational cutting head speeds have been achieved, in the range of 50,000–300,000 rmp, by these motor driven cutter heads. Various problems, however, have been associated with the use of the balloon tipped catheters and high speed cutting heads. The balloon catheter is expanded by injection of pressurized fluid into the balloon to expand it against the wall of the artery. Some problems which have been reported include the vessel dissection, perforation, rupture, conversion of a stenosis to an occlusion, and embolization. Furthermore, angioplasty devices utilizing balloons do not remove the plaque from the arterial wall but simply compress the plaque against the wall of the vessel. Thus, the stenosis or occlusion frequently reoccur requiring further treatment.

Atherectomy devices utilizing a motor driven high speed cutting head include a number of disadvantages. Heat dissipation and vibration is a problem. The path of the occlusion in an artery is often a tortuous path and therefore the lengthy flexible drive shaft connected to the cutter head must traverse a number of bends or curves. Consequently, as the flexible drive shaft rotates, it contacts the inner wall of the catheter resulting in localized heating and vibrations due to the frictional contact. This, of course, is very uncomfortable for the patient and may result in spasm, weakening or perforation of the vessel along the route of the catheter.

It is therefore one advantage of the present invention to provide an improved atherectomy catheter having a reciprocal rotary cutter head at the distal end thereof rotated at a relatively low speed in the range of 2,000 rpm to enhance patient comfort.

Various prior art devices include a catheter having a side opening slot formed in the cutter housing. Typically, the side opening slot is on the outer surface of the cutter housing thereby exposing the interior wall of the blood vessel to possible abrasion when normal variations in the vasculature are encountered by the side opening slot on the cutter housing. Additionally, aspiration through prior art catheters is restricted or limited by the size of the slot formed in the cutter housing.

It is therefore an object of the present invention to provide an improved atherectomy catheter having a cutting window which may be fully closed as the catheter is advanced through the blood vessel to the site of the occlusion. Additionally, the improved atherectomy catheter of the invention is provided with an adjustable side opening cutting window and an enlarged aspiration channel at the point of cutting thereby aiding the aspiration of severed material.

It is still another object of the invention to provide an adjustable side opening cutting window by slidable adjusting the outer sheath of the catheter to expose the desired opening.

It is yet another object of the invention to provide an atherectomy catheter for progressively opening the lumen of a vessel and discharging the excised obstructive material into a discharge passage of the catheter until the entire obstruction has been removed leaving a smooth fissure and flap-free enlarged internal vessel diameter.

SUMMARY OF THE INVENTION

A distal atherectomy catheter is disclosed for removing obstructions, plaque, stenosis, occlusions, or the like from an artery or coronary vessel. The catheter comprises a flexible, hollow catheter tube. A cutting element is located within a cylindrical housing mounted at the distal end of the catheter tube. The cutting element is connected to a hollow, flexible drive shaft concentrically located within the catheter tube. A cutter axial guide provides rotational stabilization for the cutting element. The cutting element housing includes a side opening window or port providing access to the interior of the housing. An idler shaft journaled about the drive shaft provides a non-rotating surface adjacent the cutting element. An annular return passage is defined between the catheter tube and the flexible drive shaft providing a discharge passage communicating with external aspirating means for collection of cuttings removed by the cutting element from the artery or coronary vessel. A guide wire may extend through the catheter tube and cutting element for guiding the catheter to the occluded site in a vessel. The drive cable is connected to a drive motor housed within a handle housing. The catheter tube and cutter housing are enclosed within a sheath extending from the distal end of the catheter to the handle.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is a partially broken away side view of the atherectomy catheter of the invention;

FIG. 6 is a partial sectional view sheath detent location mechanism of the invention;

FIG. 7 is a partial sectional view of the sheath of the invention in its retracted position;

FIG. 8 is a partial sectional view of the cutting head assembly of the invention and showing the sheath retracted to expose the side opening cutting window;

FIG. 9 is a partial sectional view of the cutting head assembly of the invention fully enclosed within the sheath;

FIG. 10 is a partial side view of the sheath of the invention incorporating a fiber optic lumen along the length thereof;

FIG. 11 is an end view of the sheath of the invention taken along line 11—11 of FIG. 10;

FIG. 12 is a partial sectional view showing another alternate embodiment of the cutting element of the invention;

FIG. 13 is a partial sectional view of another alternate embodiment of the cutting element of the invention; and FIG. 14 is a partial sectional view of another alternate embodiment of the cutting element of the invention.

DETAILED DESCRIPTION OF THE PREFERRED EMBODIMENT

Figure 2:
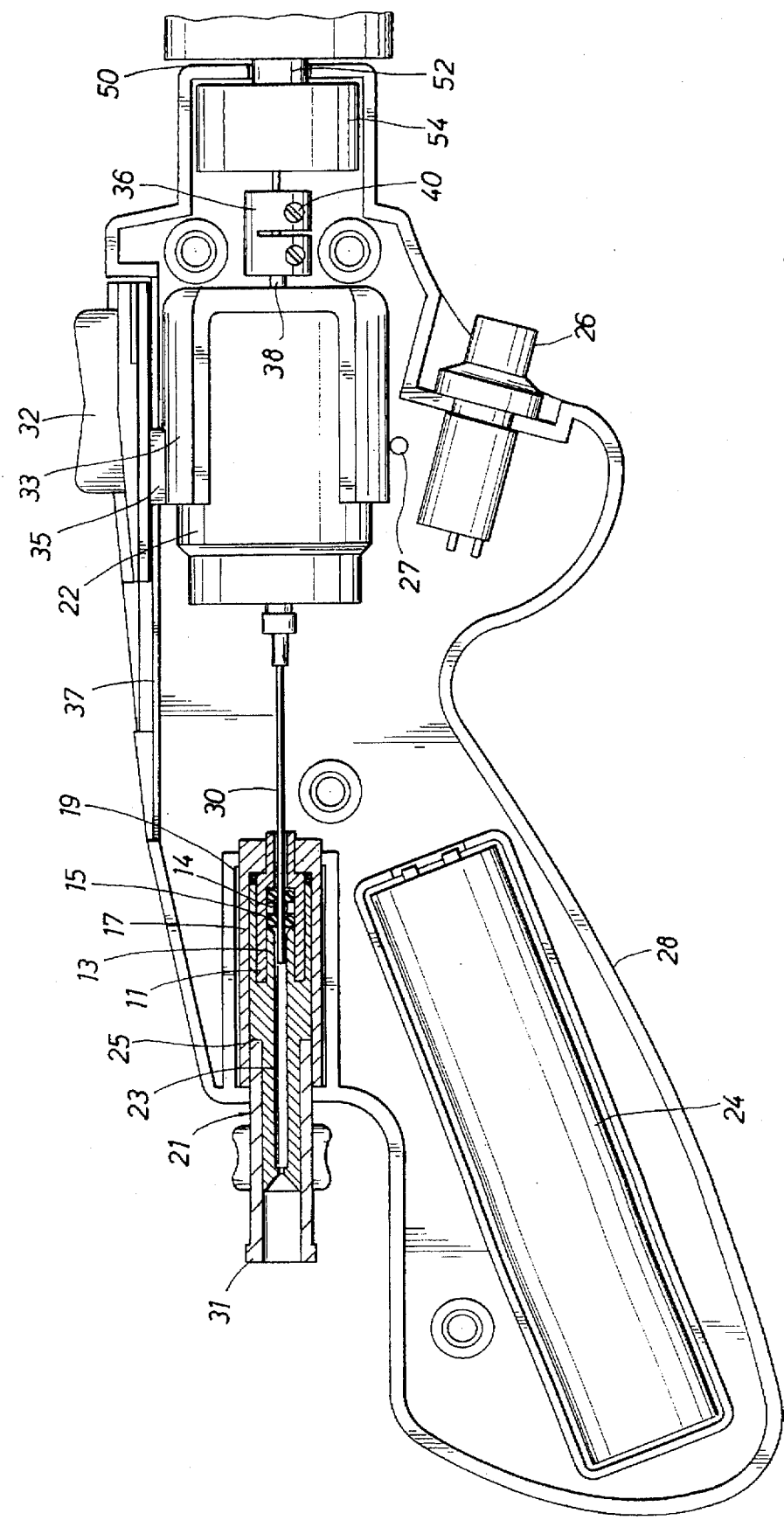
FIG. 2 is a partial sectional view of the handle of the invention.

Referring first to FIG. 1, the distal atherectomy catheter of the invention is generally identified by the reference numeral 10. The catheter 10 of the invention comprises a flexible catheter tube 12 which may be several feet in length enclosed by a sheath 12 which extends from the distal end or tip 16 of the catheter tube 12 to a handle assembly 20. The proximal end of the catheter tube is connected to the hand-held drive motor assembly generally identified by the reference numeral 20.

Referring now to FIG. 2, the handle assembly 20 is shown in greater detail. The handle assembly 20 includes a motor 22, a battery or storage cell 24 and an on-off switch 26 housed within an ergonomically designed housing 28. The motor 22, battery 24 and switch 26 are securely retained within the housing 28 and are electrically connected to provide sufficient power to operate the catheter 10. An LED bulb 27 projects through the side of the housing 28 opposite the view shown in the drawing. The LED 27 provides a visual indication when the motor is switched on by depressing the switch 26.

A drive shaft 30 extends axially from the motor 22. The drive shaft 30 extends through the motor 22 and is supported by a bushing 34 located in the rear wall of the housing 28 so that the drive shaft 30 rotates freely and shaft vibration is minimized. A coupling 36 connects the drive shaft 30 to the motor drive shaft 38. Set screws 40 extending into the coupling 36 fixedly secure the drive shaft 30 to the motor drive shaft 38 for establishing a rotary connection between the drive shaft 30 and the rotary drive motor 22.

The motor 22 and the drive shaft 30 are fixedly secured by the coupling 36 and reciprocate together within the housing 28 upon actuation of a slide button 32. The motor 22 is connected to the slide 32 by a motor mount bracket 33 which extends about the motor 22. A screw connector or the like secures the bracket 33 to the motor 22. The bracket 33 is connected to the slide button 32 by a connector 35 which extends through a slot in the top wall 37 of the housing 28, thereby enabling the motor 22 and drive shaft 30 to be jointly reciprocated within the housing 28 upon thumb actuation of the slide button 32.

Referring still to FIG. 2, a syringe adapter 21 is press fit into a rear wall 19 of the handle housing 28. The adapter 21 permits a syringe (not shown in the drawings) to be connected to the catheter 10 for delivery of fluids, such as medication, through the hollow drive shaft 30 to the site of the occulusion. The adaptor 21, frictionally retained within the recess 19 by a bushing 17, includes a compression sleeve 23 axially positioned within the adaptor 21.

The compression sleeve 23 includes a circumferential shoulder 25 which engages the forward end of the adaptor 110, thereby preventing separation of the compression sleeve 23 from the adaptor 21 and bushing 17 The forward end of the compression sleeve 23 engages an O-ring seal 29 which is journaled about the drive shaft 30. The drive shaft 30 extends through the compression sleeve 23 and the adaptor 21. The compression sleeve 23 is journaled about the drive shaft 30 and during normal use, the drive shaft 30 rotates freely within the sleeve 23. In the event delivery of medication through the catheter 10 is required, a syringe is connected to the end 31 of the adaptor 21.

A fluid tight seal around the drive shaft 30 is further accomplished by a seal assembly received within the distal end of the compression sleeve 23. The seal assembly includes seal retainer 11, seal insert 13 and a pair of quad rings 15 separated by a spacer 14.

Referring now to FIG. 2, the housing 28 is closed at its forward end by a by a cylindrical hub 49 terminating at a wall 50. The wall 50 includes an opening extending therethrough for receiving the rearward extension 52 of a catheter retainer assembly 53. The end of the extension 52 terminated in an enlarged retainer 54 received within the cylindrical hub 49 of the housing 28.

Figures 3, 4, 5:
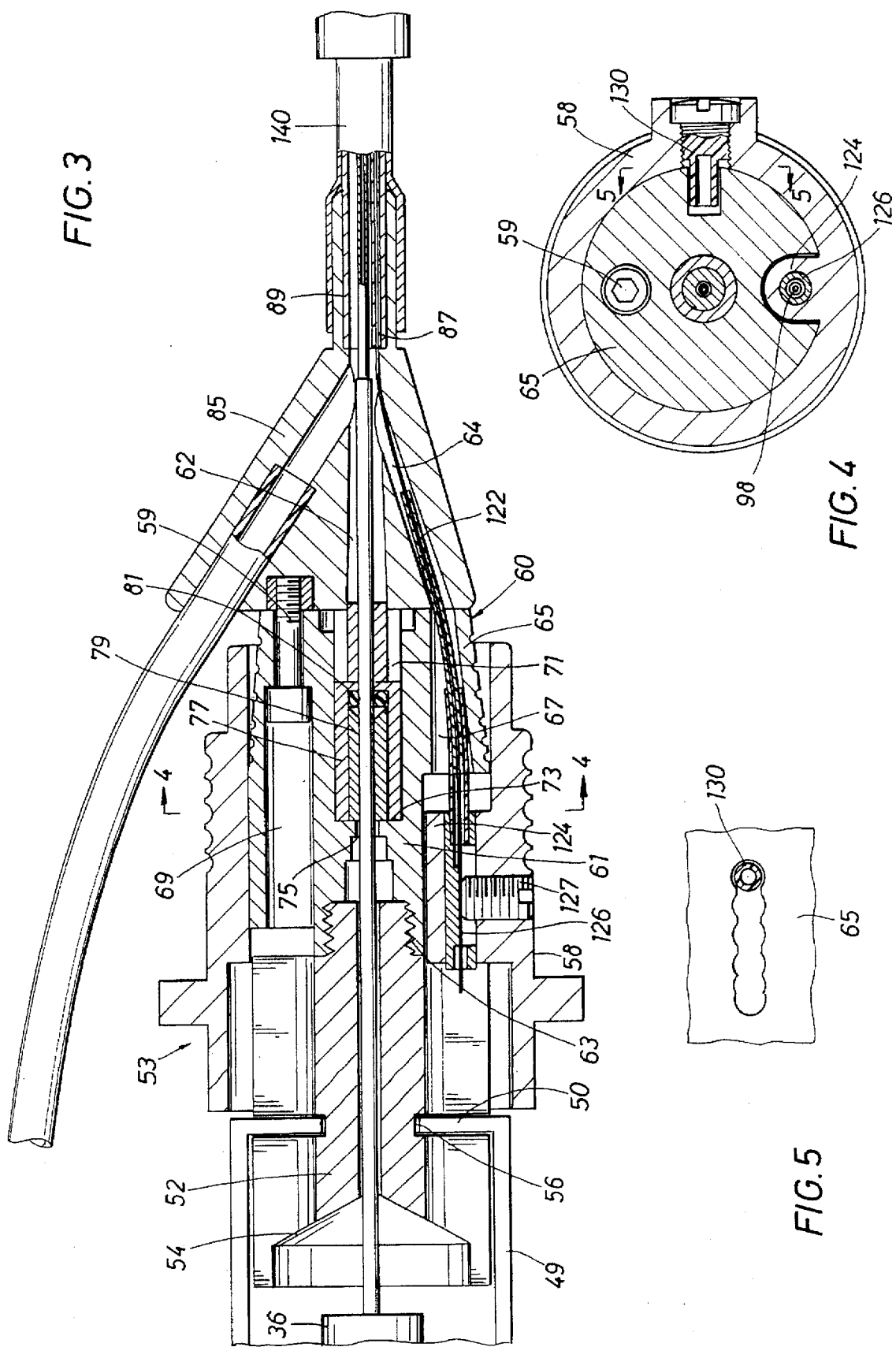
FIG. 3 is a partial sectional view wire actuation assembly of the invention.
FIG. 4 is a sectional view of the wire actuation assembly of the invention taken along line 4—4 of FIG. 3.
FIG. 5 is a partial sectional view of taken along line 5—5 of FIG. 4 showing the detent location mechanism for the wire actuation assembly of the invention.

Referring now to FIG. 3, it will be observed that the extension 52 is provided with a circumferential slot 56 for receiving the edge of the wall member 50 therein for securing the catheter retainer assembly 53 to the handle 20. The catheter retainer assembly 53 and the handle 20 are not locked together, but are pivotally connected permitting the handle 20 to be rotated about the extension 52. Thus, a surgeon using the catheter 10 may adjust the orientation of the handle 20 to comfortably hold it in his hand even while inserting the catheter tube of the invention in the patient.

The catheter retainer assembly 53 includes a wire actuation ring 58 and a front seal housing 60. The wire actuation ring 58 is slidable mounted about the seal housing 60. The seal housing 60 includes an axial stem 61 threaded at its proximal end 63 for connection to the extension 52. The distal end 65 of the housing 60 includes drilled holes 67 and 69 open at each end. The central portion of the seal housing 60 is provided with an axial seal recess 71. The recess 71 terminates at circumferential shoulder 73 which circumscribes an opening 75. Received within the recess 71 is front seal assembly comprising a seal retainer 77, a seal insert 79 and a quad seal 81. The seal retainer 77 includes an axial bore for receiving the quad seal 81 and the seal insert 79 therein. The seal retainer 77 is press fit into the recess 71 in abutting contact with the shoulder 73 of the axial seal recess 71 and is frictionally retained within the recess 71.

A Y-fitting 85 is mounted to the distal end of the front seal housing 60. The Y-fitting 85 is fixedly attached to the seal housing 60 by a connecting screw 59 received in the hole 69 of the seal housing 60. The screw 59 is retained in the hole 69 by an internal shoulder engaging the head of the screw 59. An axial passage 62 extends through the Y-fitting 85. An angular passage 64 branches from the passage 62 and terminates at the hole 67 formed in the housing 60. The opposite end of the passage 64 opens into a wire lumen 87 extending longitudinally along the catheter tube 89. The wire lumen 87, as best shown in FIG. 3, terminates at an opening 91.

Referring now to FIG. 8, the cutter head assembly of the invention is shown in greater detail. The cutter head assembly includes a cylindrical cutter housing 100 mounted to the distal end of the catheter tube 89. A slot or window 102 is formed in the cutter housing 100 providing access to the interior of the housing 100. A rotary cutter 104 is connected to the distal end of the hollow drive shaft 30 and is located within the housing 100. The cutter 104 is substantially cylindrical in shape and partially hollow. The distal end of the drive shaft 30 is embedded or bonded to the rear wall 106 of the cutter 104. An idler shaft 108 is journaled about the drive shaft 30 adjacent to the cutter 104. The idler shaft 108 is rotationally independent from the drive shaft 30 and cutter 104; it is not rotationally connected to the drive shaft 30 or the cutter 104. The idler shaft 108 provides a non-rotating surface in the vicinity of the cutter 104 so that tissue or material cut by the cutter 104 does not wrap around the drive shaft 30 and become entwined therewith. Axial movement of the idler shaft 108 along the drive shaft 30 is limited by retaining collars 110 and 112 mounted on the drive shaft 30. The retaining collars 110 and 112 are bonded on the drive shaft 30. Alternatively, the drive shaft 30 may be provided with integral retaining shoulders to prevent axial travel of the idler shaft 108.

Rotational stabilization of the cutter 104 is enhanced by a cutter axial guide shaft 114 which extends from a barbed brushing 116 mounted at the distal end of the cutter housing 100. The cutter guide shaft 114 is hollow and sized to be received within the hollow drive shaft 30. The cutter guide shaft 114 is of sufficient length to provide support for the cutter 104 over its full range of movement so that reciprocal movement of the cutter 104 does not disengage or separate it from the guide shaft 114 when the cutter 104 is retracted within the housing 100.

The proximal end of the cutter 104 forms a serrated cutting edge 118 for removing occlusive material, such as plaque which coats the arterial wall. To aid the efficiency of the cutter 104, bowed wires 98 are provided for moving the cutter housing 100 laterally against the interior arterial wall of an artery or blood vessel. The bowed wires 98 are connected to the forward tip of the cutter housing 100 at 120 and extend exterior of the cutter housing 100. The wires 98 extend the full length of the catheter tube 89 and are connected to the wire actuation ring 58 which is manipulated back and forth to actuate the wires 98 thereby moving the housing 100 laterally against the arterial wall.

The wires 98 extend back to the wire actuation ring 58 through the wire lumen 87 of the catheter tube 89. As best shown in FIG. 3, the wires 98 pass through the branched passage 64 and hole 67 in the seal housing 60 and are anchored to the actuation ring 58. A tubular guide 122 extending from the passage 64 through the hole 67 and connected to the actuation ring 58 provides a smooth passage for the wires 98.

The wire anchoring assembly comprise connector tab 124 extending inwardly from the body of the ring 58. The tab 124 supports an anvil 126 press fit within an axial recess in the tab 124. The anvil 126 includes is hollow so that the wires 98 extend through the anvil 126. A set screw 127 anchors the wires 98 to the wire actuation ring 58. A compression disk 128 is interposed between the set screw 127 and the wires 98 for firmly securing the wires 98 between the set screw 127 and the anvil 126.

Referring briefly now to FIGS. 3–5, it will be noted the actuation ring 58 includes a locator pin 130 cooperating with series of detents 132 formed in the end 65 of the seal housing 60 to aid the surgeon in controlling the lateral displacement of the cutter housing 100. This permits the cutter head assembly to be correctly positioned against the wall of the artery or blood vessel. In operation, as the wire actuator 58 is moved forward, the wires 98 extend into the artery and spread outwardly slightly so that the cutter head assembly is centrally located between the spread wires 98. The detents 132 enable the surgeon to determine the degree of lateral movement of the cutter housing 100. The surgeon hears or feels the movement of the pin 130 through the detents 132. For example, three "clicks" may represent that the wires are fully extended and maximum lateral displacement of the cutter housing 100 has been accomplished.

Referring now to FIGS. 6 and 7, the connection of the sheath 15 to the seal housing 60 is shown in greater detail. A connector extension 140 is bonded to the Y-fitting 85. The extension 140 encloses stub extension 142 integrally formed with Y-fitting 85 and is bonded thereto. The distal end 144 of the extension 140 is received and bonded to a recess coupling forming the proximal end of an inner detent sleeve 146. The detent sleeve 146 is slidable received within an outer detent sleeve 148 which is connected to the proximal end of the sheath 15 at the point 150. The inner detent sleeve 146 includes a pair of recesses 152 and 154 formed on the exterior surface of the sleeve 146. The detent sleeve 148 includes a recesses 156 supporting detent button 158 therein. An o-ring 157 provides a seal between the detent sleeves 146 and 148. The outer detent sleeve 148 is enclosed within a silastic sleeve 160 which provides a nonslip gripping area and resilientcy for the detent button 158.

The sheath 15 is advanced between the open and closed positions, best shown in FIGS. 8 and 9, by gripping the silastice sleeve 160 and pulling the sheath 15 toward the handle 20 to expose the cutter housing 100. The sheath 15 is pushed to the toward the tip 16 to enclose the cutter housing within the distal end of the sheath 15.

A termination ring 162 journaled about the distal end of the sheath 15 and bonded thereon protects the sheath 15 in the event the cutter 104 inadvertantly contacts end of the sheath 15 as it is reciprocated within the cutter housing 100.

Referring now to FIGS. 12–14, alternate embodiments of the cutter 104 are shown. In some instances, the vessel obstruction may be calcified and very hard to remove. The cutters shown in FIGS. 12–14 are provided with rearward facing grinding surface for grinding away such calcified obstructions. In FIG. 12, the grinding surface is embedded with diamond chips. The embodiment of FIG. 13, utilizes helical grinder segments formed on the rearward surface of the cutter. In FIG. 14, the rearward surface of the cutter is flutted.

Referring again to FIG. 1, the use and operation of the catheter 10 will be described. The catheter 10 is typically inserted through the femoral artery of the patient and is directed by the physician to the site of the obstruction. If a guide wire is required, the guide wire is inserted through the hollow shaft 30 and out the tip 16 at the distal end of the cutter housing 100. Alternatively, the guide wire may be inserted initially and thereafter the catheter 10 is inserted over the guide wire. The catheter 10 is inserted through the femoral artery of the patient with the sheath 15 in the closed position as shown in FIG. 1 and FIG. 9. The cutting window 102 is fully closed by the sheath 15 which has been advanced forward relative to the catheter tube 89 so that the termination ring 162 of the sheath 15 abuts the barbed bushing 116. The sheath 15 provides a smooth exterior surface thereby avoiding the risk of abrading the exposed interior wall of the blood vessel as the catheter 10 is advanced to the site of the obstruction.

Upon reaching the site of the obstruction, the sheath 15 is retracted exposing the cutter housing 100. The sheath 15 may be retracted to its maximum fully opened position or to any point between the fully closed and fully opened positions. The surgeon may thus adjust the side window opening to accommodate the size of the occlusion.

Once the cutter head assembly is properly positioned, the guide wire may be removed and a vacuum pump connected to the cannula 70 connected to the Y-fitting 85 for creating a vacuum within the catheter tube 89 for aspiration of severed or excised plaque or the like as it is severed by the cutter 104. A collection vessel is connected to the cannula 70 for receipt of the aspirated cuttings.

Upon positioning the cutting head assembly of the catheter 10 for removal of an obstruction, the switch 26 is depressed so that power is applied by the battery 24 to rotate the drive shaft 30. If desired, prior to activating the catheter 10, the site may be irrigated with fluid and/or medication which may be injected through the hollow shaft 30.

Upon actuation of the catheter 10, the shaft 30 is rotated by the motor 22. Cutting is accomplished by positioning the cutter housing 100 so that the obstructive material projects through the opening 102 into the cutter housing 100, and simultaneously rotating and reciprocating the cutter 104 within the housing 100 thereby severing tissue or the like to open the blood vessel lumen. Complete opening of the lumen may be accomplished by lateral displacement of the housing 100 moving it is against the wall of the blood vessel so that the cutter 104 completely removes the obstruction in the blood vessel. Upon removal of the obstruction, the catheter 10 may be advanced further into the blood vessel or withdrawn if further treatment is not necessary.

Referring now to FIGS. 10 and 11, a fiber optics lumen 142 is shown extending along the sheath 15 opposite the deflector wire lumen 87 in the catheter tube 89. Fiber optics permit the surgeon to see the size of the obstruction and adjust the opening 102 to the size of the obstruction. Thus, on a single pass the cutter 104 may be moved through the obstruction for removing a substantial portion of the obstruction; thereby reducing the number of passes of the cutter 104 required to fully open the lumen of the blood vessel. Additionally, a sonic array or rotating ultra sound transducer 144 may be mounted about the distal end of the sheath 15.

While the foregoing is directed to the preferred and illustrated embodiments of the invention, other and further embodiments of the invention may be devised without departing from the basic scope thereof, the scope thereof is determined by the claims which follow.

What is claimed is:

1. An atherectomy catheter for removal of occlusive material in a blood vessel, tract, or cavity comprising:

(a) a catheter tube;

(b) a cutter head assembly attached to the distal end of said catheter tube;

(c) a slidably adjustable sheath extending about and enclosing said catheter tube and said cutter head assembly;

(d) a flexible, hollow drive shaft extending through said catheter tube;

(e) a rotary cutter mounted within said cutter head assembly and connected to said flexible drive means;

(f) power means connected to the end of said catheter tube for rotating said cutter within said cutter head assembly for excising material blocking the blood vessel;

(g) an idler sleeve journaled about said drive shaft adjacent said rotary cutter; and (h) means connected to said catheter tube for evacuating the excised material from the blood vessel through said cutter head assembly and said catheter tube.

2. The apparatus of claim 1 further including means cooperative with said cutter head assembly for moving said cutter head assembly laterally, and wherein a portion of said cutter head assembly includes a window opening for occlusive material to project therethrough for removal by said rotary cutter.

3. The apparatus of claim 1 including deflector means for laterally deflecting said cutter head assembly against the occlusive material blocking the blood vessel.

4. The apparatus of claim 1 wherein said rotary cutter has rearwardly facing cutting means for cutting material obstructing the blood vessel.

5. The apparatus of claim 1 wherein said cutter head assembly is generally cylindrical in shape centered along and around an axis of rotation therethrough, and said cutter head assembly includes an axial guide shaft for guiding said rotating cutter in reciprocating fashion forwardly and rearwardly thereof to form a cutting action.

6. The apparatus of claim 2 including means for adjusting the length of said window opening to accommodate obstructive materials of various lengths.

7. The apparatus of claim 2 including an enlarged aspiration channel formed by said sheath and said catheter tube adjacent said window opening.

8. The apparatus of claim 1 including a retaining collar mounted on said drive shaft spaced from each end of said idler sleeve for limiting axial movement of said idler shaft along said drive shaft.

9. The apparatus of claim 1 including detent sleeve means slidably connecting said sheath about said catheter tube.

10. The apparatus of claim 1 wherein said rotary cutter includes a rearward facing grinding surface embedded with diamond chips.

11. The apparatus of claim 1 wherein said rotary cutter includes rearward facing helical grinder segments.

12. The apparatus of claim 1 wherein said rotary cutter includes a rearward facing flutted surface.

13. The apparatus of claim 1 wherein said sheath includes a fiber optics lumen extending the length thereof.

14. The apparatus of claim 1 wherein said sheath includes a sonic array mounted about the distal end of said sheath.

15. An atherectomy catheter for removal of occlusive material in a blood vessel, tract, or cavity comprising:

(a) a catheter tube;

(b) a cutter head assembly attached to the distal end of said catheter tube;

(c) a slidably adjustable sheath extending about and enclosing said catheter tube and said cutter head assembly;

(d) a flexible, hollow drive shaft extending through said catheter tube;

(e) a rotary cutter mounted within said cutter head assembly and connected to said flexible drive means;

(f) power means connected to the end of said catheter tube for rotating said cutter within said cutter head assembly for excising material blocking the blood vessel;

(g) an idler sleeve journaled about said drive shaft adjacent said cutter, said idler sleeve located between spaced stop collars mounted about said drive shaft;

(h) detent sleeve means slidably connecting said sheath about said catheter tube; and (i) means connected to said catheter tube for evacuating excised material from the blood vessel.

16. The apparatus of claim 15 wherein said sheath includes a fiber optics lumen extending the length thereof.

17. The apparatus of claim 15 wherein said sheath includes a sonic array mounted about the distal end of said sheath.

* * * * *